United States Patent
Sacha

(10) Patent No.: US 11,771,343 B2
(45) Date of Patent: *Oct. 3, 2023

(54) FALL DETECTION USING PHOTOPLETHYSMOGRAPHY DETECTORS IN EAR-WEARABLE DEVICES

(71) Applicant: Starkey Laboratories, Inc., Eden Prairie, MN (US)

(72) Inventor: Michael Karl Sacha, Chanhassen, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/737,691

(22) Filed: May 5, 2022

(65) Prior Publication Data

US 2022/0369954 A1 Nov. 24, 2022

Related U.S. Application Data

(63) Continuation of application No. 16/230,110, filed on Dec. 21, 2018, now Pat. No. 11,324,422.

(51) Int. Cl.
*A61B 5/11* (2006.01)
*A61B 5/024* (2006.01)
*A61B 5/00* (2006.01)

(52) U.S. Cl.
CPC ........ *A61B 5/1117* (2013.01); *A61B 5/02427* (2013.01); *A61B 5/6815* (2013.01)

(58) Field of Classification Search
CPC .. A61B 5/1117; A61B 5/02427; A61B 5/6815
See application file for complete search history.

(56) References Cited

U.S. PATENT DOCUMENTS

| 8,475,370 | B2 | 7/2013 | McCombie et al. |
| 8,585,602 | B2 | 11/2013 | Crabtree et al. |
| 9,773,397 | B2 | 9/2017 | Ten Kate et al. |
| 11,324,422 | B2 | 5/2022 | Sacha |
| 2007/0197881 | A1 | 8/2007 | Wolf et al. |
| 2008/0177162 | A1* | 7/2008 | Bae ............ A61B 5/6838 600/323 |
| 2010/0298661 | A1 | 11/2010 | McCombie et al. |
| 2012/0253156 | A1 | 10/2012 | Muhlsteff |

(Continued)

FOREIGN PATENT DOCUMENTS

| CN | 106293023 | 1/2017 |
| CN | 106293024 | 1/2017 |

(Continued)

OTHER PUBLICATIONS

File History for U.S. Appl. No. 16/230,110 downloaded Jun. 29, 2022 (262 pages).

(Continued)

*Primary Examiner* — Mohamed Barakat
(74) *Attorney, Agent, or Firm* — Pauly, DeVries Smith & Deffner LLC

(57) ABSTRACT

An ear-wearable device includes a photoplethysmography (PPG) sensor. One or more processors of the ear-wearable device are configured to determine, based on sample values of a PPG signal generated by the PPG sensor, whether a user of the ear-wearable device has fallen.

18 Claims, 5 Drawing Sheets

(56) References Cited

U.S. PATENT DOCUMENTS

| | | | |
|---|---|---|---|
| 2014/0191863 A1* | 7/2014 | Ten Kate | A61B 5/1116 340/539.12 |
| 2015/0164437 A1* | 6/2015 | McCombie | A61B 5/1117 600/301 |
| 2015/0257662 A1 | 9/2015 | Lee et al. | |
| 2016/0094899 A1* | 3/2016 | Aumer | A61B 5/6802 340/870.07 |
| 2017/0079578 A1 | 3/2017 | Van Den Broek et al. | |
| 2017/0095215 A1* | 4/2017 | Watson | A61B 5/0002 |
| 2017/0172465 A1 | 6/2017 | Osorio | |
| 2018/0177416 A1* | 6/2018 | Church | A61B 5/6815 |
| 2019/0286233 A1* | 9/2019 | Newberry | A61B 5/6825 |
| 2020/0196914 A1 | 6/2020 | Sacha | |

FOREIGN PATENT DOCUMENTS

| | | |
|---|---|---|
| WO | 2009147597 | 12/2009 |
| WO | 2010108287 | 9/2010 |
| WO | 2011077294 | 6/2011 |

OTHER PUBLICATIONS

File History for European Patent Application No. EP19212657.1 downloaded Jun. 29, 2022 (180 pages).

"Photoplethysmogram," Wikipedia, the Free Encyclopedia, accessed on Oct. 1, 2018, 4 pp.

Leake, et al. "Is pholoplethysmography-derived pulse shape useful for fall detection?," Pervasive Technologies Related to Assistive Environments, May 27-30, 2014, 8 pp.

Leake, Jason Llewellyn "Fall Detectors for People with Dementia," University of Bath Student Thesis, Jun. 2016 (364 pages).

Zheng, et al. "Effect of postural changes on lower limb blood volume, detected with non-invasive photoplethysmography," Journal of Medical Engineering & Technology, vol. 32, No. 5, Sep./Oct. 2008, pp. 358-364 (7 pages).

* cited by examiner

FALL DETECTION USING PHOTOPLETHYSMOGRAPHY DETECTORS IN EAR-WEARABLE DEVICES

This application claims the benefit of U.S. patent application Ser. No. 16/230,110, filed Dec. 21, 2018, the content of which is herein incorporated by reference in its entirety.

FIELD

This disclosure relates to ear-wearable devices.

BACKGROUND

Falls are a leading cause of accidental death and significant injury. When a person suffers an injury resulting from a fall, the person may be unable to reach a location where the person is able to request medical assistance. Accordingly, devices have been developed to automatically alert first responders that a person has suffered a fall. However, when such a device fails to report that a person has fallen, the person's injuries may worsen, or the person may die. At the same time, when a device reports that a person has fallen but the person did not actually fall, resources of first responders may be wasted.

SUMMARY

This disclosure describes an ear-wearable device having a photoplethysmography (PPG) sensor. The ear-wearable device may determine, based on a signal from the PPG sensor, whether a user of the ear-wearable device has fallen. The use of the signal from the PPG sensor to determine whether the user has fallen may reduce over- and under-reporting of falls.

In one example, this disclosure describes an ear-wearable device comprising: a photoplethysmography (PPG) sensor; and one or more processors configured to determine, based on sample values of a PPG signal generated by the PPG sensor, whether a user of the ear-wearable device has fallen.

In another example, this disclosure describes a method for detecting whether a user of an ear-wearable device has fallen, the method comprising: obtaining, by one or more processors of an ear-wearable device, sample values of a photoplethysmography (PPG) signal generated by a PPG sensor of the ear-wearable device; determining, by the one or more processors, based on the sample values of the PPG signal, whether the user of the ear-wearable device has fallen; and outputting, by the ear-wearable device, an alert in response to determining that the user has fallen.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

In accordance with the techniques of this disclosure, an ear-wearable device may include a photoplethysmography (PPG) sensor. One or more processors of the ear-wearable device may determine, based on sample values of a PPG signal generated by the PPG sensor, whether a user of the ear-wearable device has fallen. The PPG signal may correspond to the user's blood perfusion at a location illuminated by a light source of the PPG sensor (i.e., the user's local blood perfusion). The user's local blood perfusion may be correlated with the user's blood pressure at the location illuminated by the light source of the PPG sensor. Due primarily to the force of gravity acting on the user's blood, the local blood perfusion in the user's ear is generally less when the user is standing than the local blood perfusion in the user's ear when the person is lying prone. Thus, a sudden increase in the user's local blood perfusion may correspond to the user experiencing a fall.

Figure 1:
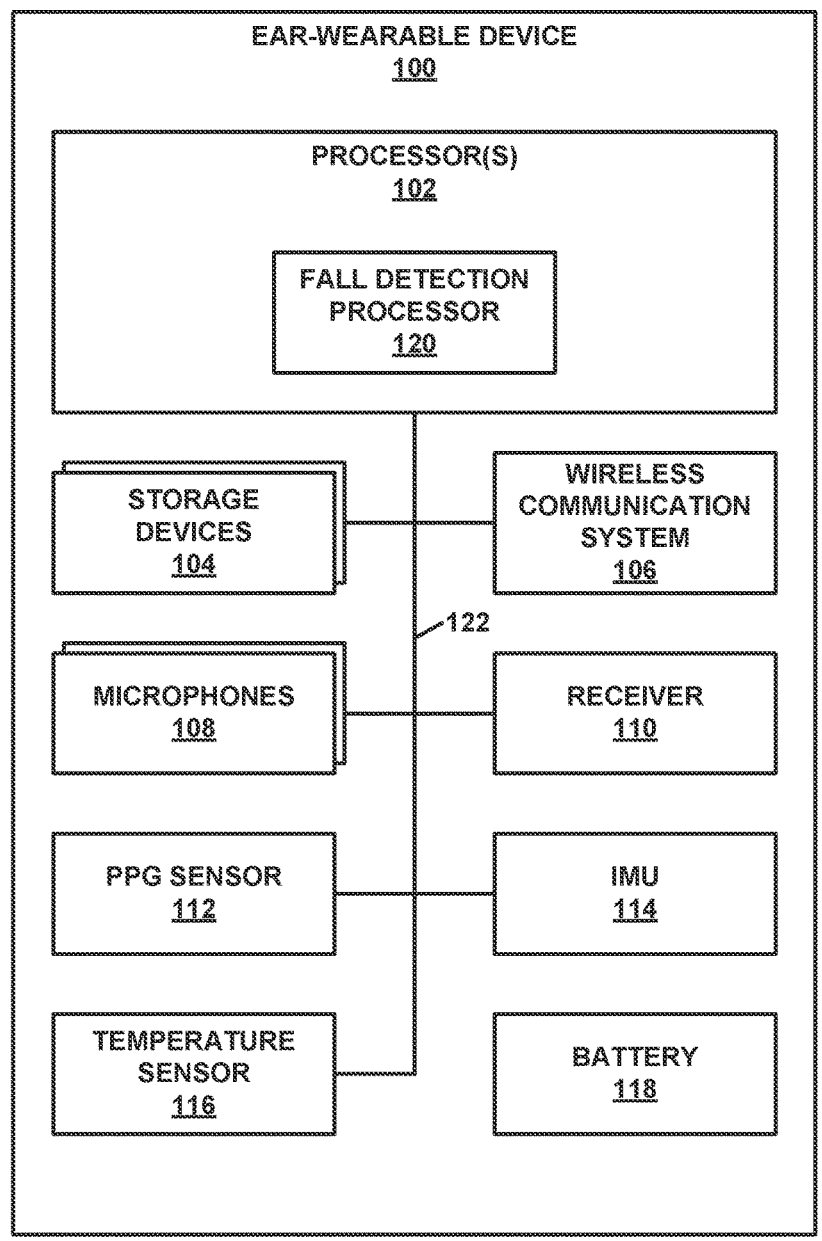
FIG. 1 illustrates an example ear-wearable device in accordance with one or more techniques of this disclosure.

FIG. 1 is a block diagram illustrating example components of ear-wearable device 100 configured according to one or more techniques of this disclosure. In the example of FIG. 1, ear-wearable device 100 includes one or more processors 102, storage device(s) 104, a wireless communication system 106, one or more microphones 108, a receiver 110, a photoplethysmograph (PPG) sensor 112, an inertial measurement unit (IMU) 114, a temperature sensor 116, a battery 118, and one or more communication channels 122. Communication channels 122 provide communication between processors 102, storage device(s) 104, wireless communication system 106, microphones 108, receiver 110, PPG sensor 112, and IMU 114. Processors 102, storage devices 104, wireless communication system 106, receiver 110, PPG sensor 112, and IMU 114 may draw electrical power from battery 118, e.g., via appropriate power transmission circuitry. In other examples, ear-wearable device 100 may include more, fewer, or different components. For instance, in some examples, ear-wearable device 100 may include additional sensors. In some examples, ear-wearable device 100 does not include IMU 114 and/or temperature sensor 116.

Ear-wearable device 100 may belong to one of various types of ear-wearable devices. For example, ear-wearable device 100 may be a Receiver-In-Canal (RIC) hearing aid, an In-The-Ear (ITE) hearing aid, an In-The-Canal (ITC) hearing aid, a Completely-In-Canal (CIC) hearing aid, an Invisible-In-The-Canal (IIC) hearing aid, or another type of hearing aid. In other examples, ear-wearable device 100 is an earphone, earbud, or other type of device designed to be worn on or in a user's ear.

In examples where ear-wearable device 100 is a MC hearing aid, ear-wearable device 100 may comprise a behind-the-ear unit and an in-ear unit connected by a cable. In such examples where ear-wearable device 100 is a MC hearing aid, the components of ear-wearable device 100 shown in FIG. 1 may be divided among the behind-the-ear unit and the in-ear unit. For instance, the in-ear unit may contain receiver 110 and PPG sensor 112 and the behind-the-ear unit may contain the remaining components of ear-wearable device. Other divisions of components among the behind-the-ear unit and the in-ear unit are possible in ear-wearable devices that implement the techniques of this disclosure. For instance, in some examples, the in-ear unit may contain one or more of processors 102 and the behind-the-ear unit may contain one or more other ones of processors 102.

Processors 102 of ear-wearable device 100 include processing circuits for processing information. Processors 102 may include general-purpose microprocessors, digital signal processors (DSPs), application-specific integrated circuits (ASICs), field-programmable gate arrays (FPGAs), microcontroller units, and other types of circuits for processing information. In some examples, one or more of processors 102 retrieve and execute instructions stored in one or more of storage devices 104. The instructions may include software instructions, firmware instructions, or another type of computer-executed instructions. In different examples of this disclosure, processors 102 may perform the fall detection processes of this disclosure fully or partly by executing such instructions, or fully or partly in hardware, or a combination of hardware and execution of instructions. In some examples, the processes for fall detection are performed entirely or partly by processors of devices outside ear-wearable device 102A, such as by a smartphone or other mobile computing device.

In the example of FIG. 1, processors 102 include a fall detection processor 120. As described in greater detail elsewhere in this disclosure, fall detection processor 120 may determine, based at least on a signal from PPG sensor 112, whether a user of ear-wearable device 100 has fallen. Fall detection processor 120 may be implemented using any of the types of processors listed above or others. In some examples, fall detection processor 120 comprises one or more dedicated circuits for fall detection. In other examples, fall detection processor 120 include one or more more general-purpose processors that are configured to perform functions in addition to fall detection.

Storage device(s) 104 of ear-wearable device 100 include devices configured to store data. Such data may include computer-executable instructions, such as software instructions or firmware instructions. Storage device(s) 104 may include volatile memory and may therefore not retain stored contents if powered off. Examples of volatile memories may include random access memories (RAM), dynamic random access memories (DRAM), static random access memories (SRAM), and other forms of volatile memories known in the art. Storage device(s) 104 may further be configured for long-term storage of information as non-volatile memory space and retain information after power on/off cycles. Examples of non-volatile memory configurations may include flash memories, or forms of electrically programmable memories (EPROM) or electrically erasable and programmable (EEPROM) memories.

Wireless communication system 106 may enable ear-wearable device 100 to send data to and receive data from one or more other computing devices. For example, wireless communication system 106 may enable ear-wearable device 100 to send data to and receive data from another ear-wearable device, a smartphone, a wireless base station, a personal computer, a tablet computer, or another type of device configured for wireless communication. Wireless communication system 106 may use various types of wireless technology to communicate. For instance, wireless communication system 106 may use Bluetooth, 3G, 4G, 4G LTE, ZigBee, WiFi, Near-Field Magnetic Induction (NFMI), or another communication technology. In other examples, ear-wearable device 100 includes a wired communication system that enables ear-wearable device 100 to communicate with one or more other devices via a communication cable, such as a Universal Serial Bus (USB) cable or a Lightning™ cable.

Microphones 108 are configured to convert sound into electrical signals. In other words, microphones 108 may generate one or more input audio signals. In some examples, microphones 108 include a front microphone and a rear microphone. The front microphone may be located closer to the front (i.e., ventral side) of the user. The rear microphone may be located closer to the rear (i.e., dorsal side) of the user. One or more of microphones 108 are omnidirectional microphones, directional microphones, or other types of microphones. Processors 102 may generate an output audio signal based on the one or more input audio signals generated by microphones 108.

Receiver 110 includes one or more speakers for producing sound based on the output audio signal. Receiver 110 is so named because receiver 110 is the component of ear-wearable device 100 that receives signals to be converted into soundwaves. In some examples, the speakers of receiver 110 include one or more woofers, tweeters, woofer-tweeters, or other specialized speakers for providing richer sound.

As mentioned above, ear-wearable device 100 includes PPG sensor 112. PPG sensor 112 may comprise a light source, such as a light emitting diode (LED), and a photodetector. When ear-wearable device 100 is worn, the light source of PPG sensor 112 illuminates a portion of the user's skin and the photodetector of PPG sensor 112 detects changes in absorption of light transmitted or reflected by the user's skin. The changes in the absorption of the transmitted or reflected light correspond to changes in blood perfusion in the area of the user's skin illuminated by the light source of PPG sensor 112.

In some examples, PPG sensor 112 is integrated into a shell of ear-wearable device 100. For instance, the shell of ear-wearable device may define a cavity that contains one or more of the components of ear-wearable device shown in FIG. 1. In this example, the shell may define one or more openings for the light source of PPG sensor 112 and the photodetector of PPG sensor 112.

In other examples, PPG sensor 112 is outside a shell of ear-wearable device 100. For instance, if ear-wearable device 100 is a BTE device, PPG sensor 112 may be located in the user's ear and may communicate with ear-wearable device 100 via a communication cable or may communicate with ear-wearable device 100 wirelessly. In an example where ear-wearable device 100 is a RIC device, PPG sensor 112 may be incorporated into the in-ear unit of the RIC device and may communicate with the behind-the-ear unit of the RIC device via a RIC cable or may communicate with the behind-the-ear unit of the RIC device wirelessly.

PPG sensor 112 outputs a signal, which may be referred to in this disclosure as a PPG signal. The PPG signal may comprise a series of sample values. Under typical circumstances, the PPG signal is a waveform having peaks and valleys corresponding to times of maximum and minimum local blood perfusion during the user's cardiac cycle. A DC component of this waveform may correspond to a minimum volumetric measurement of blood in the area of the user's skin illuminated by the light source of PPG sensor 112. Storage devices 104 may store sample values for a rolling window of the PPG signal.

In various examples, PPG sensor 112 may be in one of various locations in and around the user's ear. For example, PPG sensor 112 may be located inside an ear canal of the user of ear-wearable device 100. Advantageously, because human ears, and especially human ear canals, have relatively dense capillary beds, PPG signals may more accurately reflect local blood perfusion when PPG sensors are positioned within users' ears than when PPG sensors are located on other parts of users' bodies. Moreover, positioning PPG sensor 112 in the user's ear may be more discrete than positioning PPG sensors elsewhere on the user's body where the skin has less dense capillary beds, such as at the user's temple or elbows. Additionally, because of the close fit of ear-wearable device 100 to the ear canal and/or concha bowl, the PPG signal generated by PPG sensor 112 may have fewer motion artifacts than a PPG signal generated by a PPG sensor on the user's wrist, which may enable PPG sensor 112 to generate a PPG signal that more accurately indicates the level of blood perfusion.

IMU 114 detects linear acceleration of ear-wearable device 100. IMU 114 may include one or more accelerometers. In some examples, IMU 114 may also include one or more gyroscopes. IMU 114 may output one or more signals that are representative of the linear acceleration of ear-wearable device 100. For instance, IMU 114 may output one or more of a first signal corresponding to acceleration in an X dimension, a second signal corresponding to acceleration in a Y dimension, a third signal corresponding to acceleration in a Z dimension, and a fourth signal corresponding to gyroscope output. This disclosure may refer to the signals output by IMU 114 as IMU signals. Storage devices 104 may store rolling windows of sample values of the one or more IMU signals.

Prior ear-wearable devices have used IMU signals to determine whether users have fallen. However, processing IMU signals to determine whether a user has fallen is complicated and prone to false triggering (i.e., over-reporting) or under-reporting. For instance, it may be difficult to distinguish based on IMU signals whether a user has fallen versus whether the user has suddenly crouched. False triggering may occur when a fall is detected, but no fall occurred. Under-reporting may occur when a fall occurs, but the fall is not detected. The consequences of false triggering may range from annoyance to a wasteful drain on the resources of first responders. Under reporting of a serious fall may be have fatal consequences. The high variability of how people fall may further complicate the interpretation of IMU signals.

The techniques of this disclosure may improve the fall detection capabilities of ear-wearable devices. As described herein, fall detection processor 120 may determine, based on sample values of a PPG signal generated by PPG sensor 112, whether a user of ear-wearable device 100 has fallen. In response to determining that the user of ear-wearable device 100 has fallen, fall detection processor 120 may cause ear-wearable device 100 to generate an alert. For example, fall detection processor 120 may cause wireless communication system 106 of ear-wearable device 100 to wirelessly send an alert message to a computing device. The alert message may notify a relevant party to assist the user. In some examples, fall detection processor 120 may output an audible prompt to the user asking the user to indicate whether the user needs help. In such examples, if the user provides a vocal indication that the user needs help or if the user does not respond to the prompt, ear-wearable device 100 may wirelessly send the alert message.

In different examples of this disclosure, fall detection processor 120 may make the determination of whether the user has fallen in one of various ways. For instance, in one example, fall detection processor 120 may determine a DC component value based on sample values of the PPG signal corresponding to successive time windows. In some examples, fall detection processor 120 may determine the DC component value by applying a discrete cosine transform to the sample values of the PPG signal corresponding to a time window. In some examples, the time windows may overlap. Fall detection processor 120 may then calculate differences between DC component values corresponding to successive time windows. If any of the differences is greater than a particular threshold value, fall detection processor 120 may determine that the user has fallen. In this way, in one example, fall detection processor 120 may determine a DC component of the PPG signal. In this example, fall detection processor 120 may determine whether the DC component of the PPG signal has changed in a particular direction (e.g., downward when lower sample values correspond to lower local blood perfusion) by the threshold amount within a time window.

In some examples, fall detection processor 120 may determine the particular threshold value based on data collected from the user. For instance, when ear-wearable device 100 is being configured for use or at another time, the user may be asked to stand and may also be asked to lie prone. Fall detection processor 120 may record PPG-based data corresponding to when the user is known to be standing and when the user is known to be lying prone. For instance, fall detection processor 120 may store (e.g., in storage devices 104) a first DC component value for when the user is standing and a second DC component value for when the user is lying prone. In this example, the particular threshold may be determined (e.g., by fall detection processor 120) based on a difference between the first DC component value and the second DC component value. For instance, the particular threshold may be set equal to the difference or a percentage of the difference (e.g., 110% of the difference, 90% of the difference, 80% of the difference, etc.).

In some examples, fall detection processor 120 may determine a PPG confidence value that indicates a level of confidence that the PPG signal indicates that the user has fallen. For example, fall detection processor 120 may determine differences between DC component values as described above and may determine the confidence value based on a mapping of differences to allowable confidence values. In some examples, fall detection processor 120 may determine, based on an AC component of the PPG signal, whether the user's heart rate has changed. A rapid rise in heart rate is associated with a fall. Accordingly, in such examples, fall detection processor 120 may increase the PPG confidence level in response to detecting a rise in the user's heart rate (e.g., by detecting that a user's heart rate has risen by a threshold percentage or amount relative to the user's baseline or prior heart rate within a threshold amount of time).

In some examples, the user's blood perfusion and heart rate may both drop after initially rising if the user is bleeding heavily from a fall. Furthermore, in the example of FIG. 1, ear-wearable device 100 may include temperature sensor 116 that measures the temperature of the user's body. If the user is bleeding heavily from a fall, the user's body temperature may drop outside a range that is typical for the user. In some examples, ear-wearable device 100 may collect data from temperature sensor 116 to establish the range of body temperatures typical for the user. Falling body temperature may especially be a sign of bleeding if fall detection processor 120 determines (e.g., based on one or more IMU signals) that the user was not previously engaged in strenuous exercise and/or that the user has not moved a significant distance from a location at which the apparent fall occurred (e.g., the user did not move outside into a cold area.)

Accordingly, fall detection processor 120 may increase the PPG confidence value if fall detection processor 120 detects a pattern of falling blood perfusion, heart rate, and/or body temperature. Furthermore, in this event, fall detection processor 120 may cause ear-wearable device 100 to output an urgent alert.

In some examples, fall detection processor 120 may determine, based on PPG signals and also IMU signals, whether the user of ear-wearable device 100 has fallen. Using both the PPG signals and the IMU signals to determine whether the user has fallen may be more robust than using only PPG signals or IMU signals alone to determine whether the user has fallen. That is, use of both PPG signals and IMU signals to determine whether the user has fallen may result in less over- and under-reporting of falls. This is because the processors may be able to use fall detections based on the PPG signal as a check on fall detections based on the IMU signals, or vice versa.

For instance, in one example, a user may suddenly move from a standing posture to a crouching posture (e.g., a greet an excited pet or child). The IMU signals may register the sudden movement from the standing posture to the crouching posture as a sudden vertical drop consistent with a fall. However, when the user moves to the crouching posture, the user's head typically remains above the user's heart. Accordingly, the user's local blood perfusion as detected by PPG sensor 112 does not change as dramatically when moving from a standing position to a crouching position. Thus, the PPG signal would not reflect a change in local blood perfusion consistent with a fall when the user suddenly moves from a standing position to a crouching position. Conversely, the PPG signal may register a sudden increase in local blood perfusion when a surprising event occurs, but without a corresponding sudden downward acceleration, fall detection processor 120 may determine that the user has not fallen. Thus, the use of both the PPG signal and the IMU signals may reduce over-reporting in different scenarios.

There are four phases of a potential fall: a pre-fall phase, an acceleration phase, a deceleration phase, and a post-fall phase. In some examples, fall detection processor 120 may determine a score for each of the four phases of the potential fall. Fall detection processor 120 may determine an overall profile of the four phases of the potential fall. For example, fall detection processor 120 may receive an IMU signal that is a sum of tri-axial acceleration signals generated by accelerometers of IMU 114. In this example, fall detection processor 120 may determine whether an IMU signal has a pattern of values that corresponds a profile of the IMU signal known to correspond to a fall. In other words, in the pre-fall phase, the IMU signal indicates little or no acceleration; in the acceleration phase, the IMU signal indicates rapid acceleration; in the deceleration phase, the IMU signal indicates rapid deceleration; and in the post-fall phase, the IMU signal indicate little or no acceleration. To determine whether the user has fallen, fall detection processor 120 may first determine whether the IMU signal indicates that there has been an acceleration above a particular threshold (e.g., within a particular percentage, such as 90%, of $9.8 \text{ m/s}^2$). If so, fall detection processor 120 may determine a first score based on a degree of difference between samples of the IMU signal occurring before the acceleration and samples in the known pre-fall phase of a fall; may determine a second score based on a degree of difference between samples of the IMU signal occurring during the acceleration and samples in the known acceleration phase of a fall; may determine a third score based on a degree of difference between samples of the IMU signal occurring immediately after the acceleration and samples in the known deceleration phase of a fall; and may determine a fourth score based on a degree of difference between samples of the IMU signal occurring later after the acceleration and samples in the known post-fall phase of a fall. In this example, fall detection processor 120 may determine a final score based on the first, second, third, and fourth scores. For instance, the final score may be a sum of the first, second, third, and fourth scores. In this example, if the sum is less than a threshold, fall detection processor 120 may determine that a fall has occurred. In some examples, the final score may be normalized to a range of 0 to 1, and 1 minus the resulting normalized value may serve as a confidence score for the IMU-based fall detection.

In some examples, fall detection processor 120 may determine, based on the IMU signals, an IMU confidence score indicating a level of confidence that the one or more IMU signals indicate that the user has fallen during a time window. In such examples, higher values of the IMU confidence score may correspond to higher confidence that the user has fallen during the time window. Furthermore, in this example, fall detection processor 120 may determine that the user has fallen if the IMU confidence score is above a first confidence threshold (e.g., 0.9, 0.95, etc.). However, if the IMU confidence score is less than the first confidence threshold and greater than a second confidence threshold, the user may have fallen but evidence from the IMU signals is inconclusive. Thus, in some examples, in situations where the IMU confidence level is between the first confidence threshold and the second confidence threshold, fall detection processor 120 may determine, based on sample values of the PPG signal, whether a fall has occurred. Determining whether the user has fallen based on the PPG signal only if the IMU confidence score falls between the first and second confidence thresholds may reduce energy consumption and reduce consumption of computational resources of ear-wearable device 100.

Conversely, in some examples, fall detection processor 120 may first determine a PPG confidence score based on the PPG signal. Fall detection processor 120 may determine an IMU confidence score based on the IMU signals if the PPG confidence score is greater than a first confidence threshold and less than a second confidence threshold. Calculating the IMU confidence score only if the PPG confidence score falls between the first and second confidence thresholds may reduce energy consumption and reduce consumption of computational resources.

In some examples, processors 102 may use the DC component of the PPG signal to determine a posture of the user. For instance, processors 102 may use the DC component of the PPG signal to determine whether the user is standing, seated, or prone. The DC component of the PPG signal may have an intermediate level when the user is seated as compared to when the user is standing and prone. In some examples, processors 102 may use one or more of the IMU signals to make the PPG-based determination of the user's posture more robust. Likewise, using the PPG signal to determine whether the user has moved between standing and sitting positions may increase the robustness of an IMU-based determination of whether the user has moved between standing and sitting positions. Processors 102 may use information about the user's posture for various purposes. For example, processors 102 may use information about the user's posture for health tracking. For instance, processors 102 may perform one or more actions (e.g., outputting a notification to the user, logging the change in posture, etc.) if the user has been sitting for an amount of time that exceeds a limit.

In some examples, a user may wear ear-wearable devices in both ears. In such examples, fall detection processor 120 may determine, based on the sample values of the PPG signal generated by PPG sensor 112 and based on information from the user's other ear-wearable device, whether the user has fallen. For instance, in one example, the user's ear-wearable devices may include a master ear-wearable device and a servant ear-wearable device. In this example, in response to determining that the user has likely fallen, a master ear-wearable device (e.g., ear-wearable device 100) may send a message (e.g., through a wired or wireless link) to a servant ear-wearable device requesting the servant ear-wearable device indicate whether the servant ear-wearable device has determined that the user has likely fallen. In this example, the servant ear-wearable device may send a response to the master ear-wearable device. If the response indicates that the servant ear-wearable device has determined that the user has likely fallen, the master ear-wearable device 100 may perform various actions, such as generating an alert, increasing a confidence score, etc. Furthermore, in some examples, because the user may lose or damage the servant ear-wearable device during a fall, the master ear-wearable device may increase the confidence score if the servant ear-wearable device does not respond or responds with an indication that the servant ear-wearable device's PPG signal and/or IMU signals are consistent with the servant ear-wearable device being away its proper position on the user's body. Similarly, if the servant ear-wearable device determines that the user has likely fallen, the servant ear-wearable device may send a message to the master ear-wearable device. If the master ear-wearable device does not respond or the master ear-wearable device's PPG signal and/or IMU signals are consistent with the master ear-wearable device being away from its proper position on the user's body, the servant ear-wearable device may start performing the role of the master ear-wearable device and may generate an alert. In other examples, the user's ear-wearable devices may perform identical fall detection operations.

Figure 2:
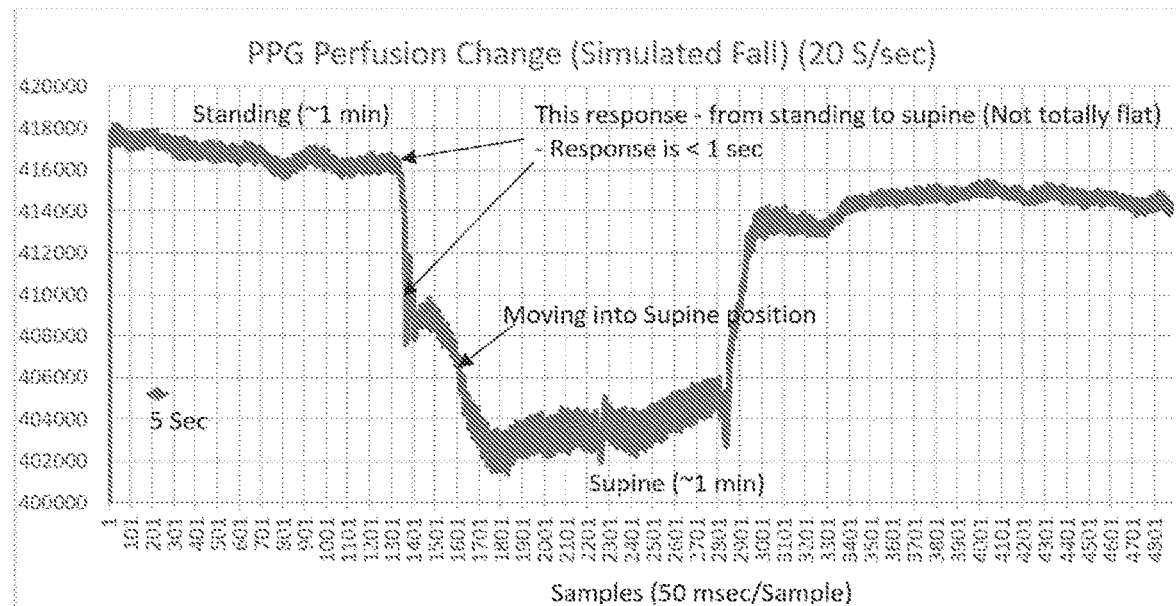
FIG. 2 is a chart showing an example photoplethysmogram obtained using a photoplethysmography (PPG) sensor when the PPG sensor is positioned in or near an ear of a user of an ear-wearable device.

FIG. 2 is a chart showing an example photoplethysmogram obtained using PPG sensor 112 when PPG sensor 112 is positioned in or near an ear of a user of ear-wearable device 100. In the example of FIG. 2, PPG sensor 112 generates sample values at a rate of 20 samples per second. Each of the sample values is a value corresponding to the detected blood perfusion in a portion of the user's skin that is illuminated by a light source of PPG sensor 112. In general, greater blood perfusion corresponds to greater local blood perfusion. It is also noted that local blood perfusion rises and falls as part of each cardiac cycle. In FIG. 2, higher values correspond to lower blood perfusion. Particularly, PPG sensor 112 may output an analog electrical signal with a voltage level corresponding to levels of detected blood perfusion. An analog-to-digital converter (ADC) of ear-wearable device 100 may convert the analog electrical signal into ADC count values. In the example of FIG. 2, values on the y-axis are ADC count values. Particularly, in the example of FIG. 2, the ADC count values has 19-bit resolution meaning that a voltage range can be divided into 524,288 voltage steps. Each of the voltage steps may be referred to as an ADC count value.

As shown in FIG. 2, when the user of ear-wearable device 100 experiences a fall, the values in the chart drop rapidly, corresponding to a rapid increase in blood perfusion in the portion of the user's skin that is illuminated by the light source of PPG sensor 112. Conversely, when the user stands back up (at a time corresponding approximately to sample 2801 in FIG. 2) the values rise again indicating a decrease in blood perfusion.

The effect of rapid increase in blood perfusion following a fall may be most apparent in the user's head. In contrast, the same increase in blood perfusion when a fall occurs may not be detected by a PPG sensor in a watch strapped to a user's wrist. Thus, the use of a PPG signal from a PPG sensor of an ear-wearable device may be uniquely suited for fall detection as compared to PPG sensors mounted elsewhere on the body. Because the people that are most likely to suffer serious harm from falls are also the most likely to use hearing aids, the use of the PPG signal from a PPG sensor of a hearing aid may obviate the need for separate fall detection devices among this population.

Figure 3:
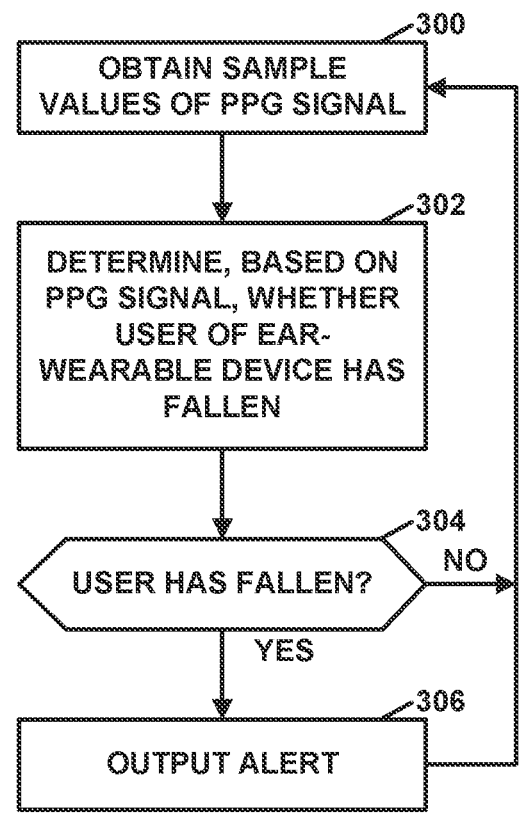
FIG. 3 is a flowchart of a first example operation of this disclosure.

FIG. 3 is a flowchart of a first example operation of this disclosure. The flowcharts of this disclosure are provided as examples. In other examples consistent with the techniques of this disclosure, operations may include more, fewer, or different actions, or actions may be performed in different orders.

In the example of FIG. 3, fall detection processor 120 may obtain sample values of a PPG signal generated by PPG sensor 112 of ear-wearable device 100 (300). In some examples, fall detection processor 120 or another one of processors 102 may write sample values of the PPG signal generated by PPG sensor 112 to one or more of storage devices 104. In such examples, fall detection processor 120 may obtain the sample values of the PPG signal by reading the sample values of the PPG signal from one or more of storage devices 104.

Furthermore, in the example of FIG. 3, fall detection processor 120 may determine, based on the sample values of the PPG signal, whether a user of ear-wearable device 100 has fallen (302). Fall detection processor 120 may make this determination in any of various ways, including those described elsewhere in this disclosure. For instance, fall detection processor 120 may determine that the user of ear-wearable device 100 has fallen based on the PPG signal indicating that the local blood perfusion of the user has risen by a threshold amount within a threshold amount of time.

In response to determining that the user has fallen ("YES" branch of 304), fall detection processor 120 may cause ear-wearable device 100 to output an alert (306). Fall detection processor 120 may cause ear-wearable device 100 to output the alert in the manner set forth in any of the examples provided elsewhere in this disclosure. However, if the fall detection processor 120 determines that the user has not fallen ("NO" branch of 304), fall detection processor 120 may continue to obtain sample values of the PPG signal (300) and determine whether the user has fallen (302).

Figure 4:
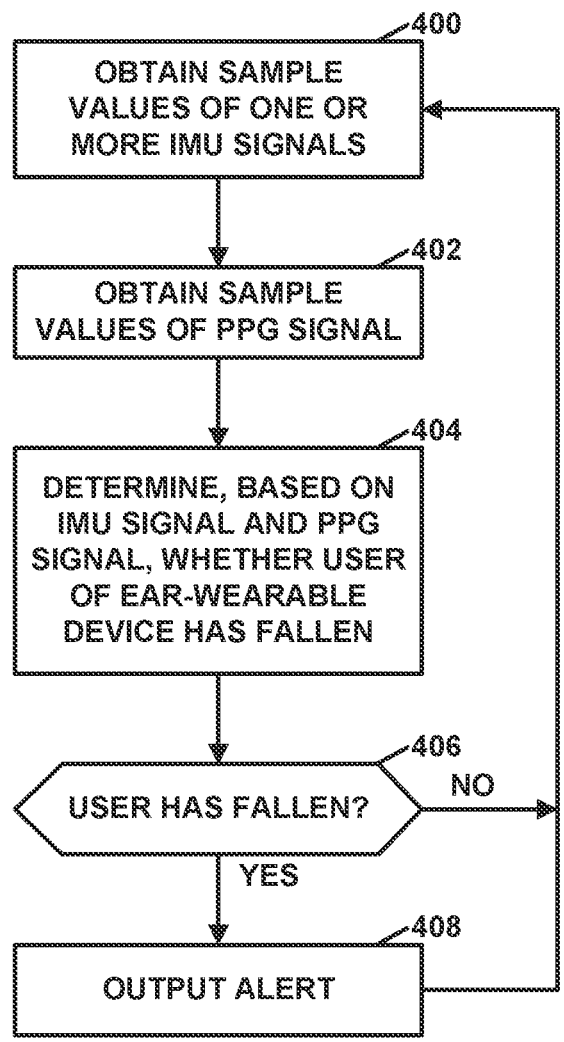
FIG. 4 is a flowchart of a second example operation of this disclosure.

FIG. 4 is a flowchart of a second example operation of this disclosure. In the example of FIG. 4, fall detection processor 120 may obtain sample values of one or more IMU signals (400). In some examples, fall detection processor 120 or another one of processors 102 may write sample values of the IMU signals generated by IMU 114 to one or more of storage devices 104. In such examples, fall detection processor 120 may obtain the sample values of the one or more IMU signals by reading the sample values of the IMU signals from one or more of storage devices 104.

Additionally, fall detection processor 120 may obtain sample values of the PPG signal (402). Fall detection processor 120 may obtain the sample values of the PPG signal in accordance with any of the examples provided elsewhere in this disclosure.

Furthermore, in the example of FIG. 4, fall detection processor 120 may determine, based in the sample values of the IMU signals and the sample values of the PPG signals, whether the user of ear-wearable device 100 has fallen (404). For example, fall detection processor 120 may determine an IMU confidence score based on the sample values of the IMU signal and a PPG confidence score based on the sample values of the PPG signal. In this example, the IMU confidence score and the PPG confidence score may each indicate a level of confidence that the user has fallen. In this example, fall detection processor 120 may determine that the user has fallen based on either or both the IMU confidence score and the PPG confidence score. For instance, in this example, fall detection processor 120 may determine that the user has fallen if both the IMU confidence score and the PPG confidence score are above certain thresholds. In some examples, fall detection processor 120 only determines the PPG confidence score if the IMU confidence score is above a threshold. In some examples, fall detection processor 120 only determines the PPG confidence score if the PPG confidence score is above a threshold.

In another example, fall detection processor 120 may make a binary determination based on the PPG signal that a user has fallen if the user's local blood perfusion has risen by a particular amount within a particular time window. In this example, fall detection processor 120 may also make a binary determination based on the IMU signal whether the user has fallen. In this example, if both the determination based on the PPG signal and the determination based on the IMU signal are that the user has fallen, fall detection processor 120 may determine that the user has fallen.

In response to determining that the user has fallen ("YES" branch of 406), fall detection processor 120 may cause ear-wearable device 100 to output an alert (408). Fall detection processor 120 may cause ear-wearable device 100 to output the alert in accordance with any of the examples provided elsewhere in this disclosure. However, in response to determining that the user has not fallen ("NO" branch of 406), fall detection processor 120 may repeat actions (400) through (404).

Figure 5:
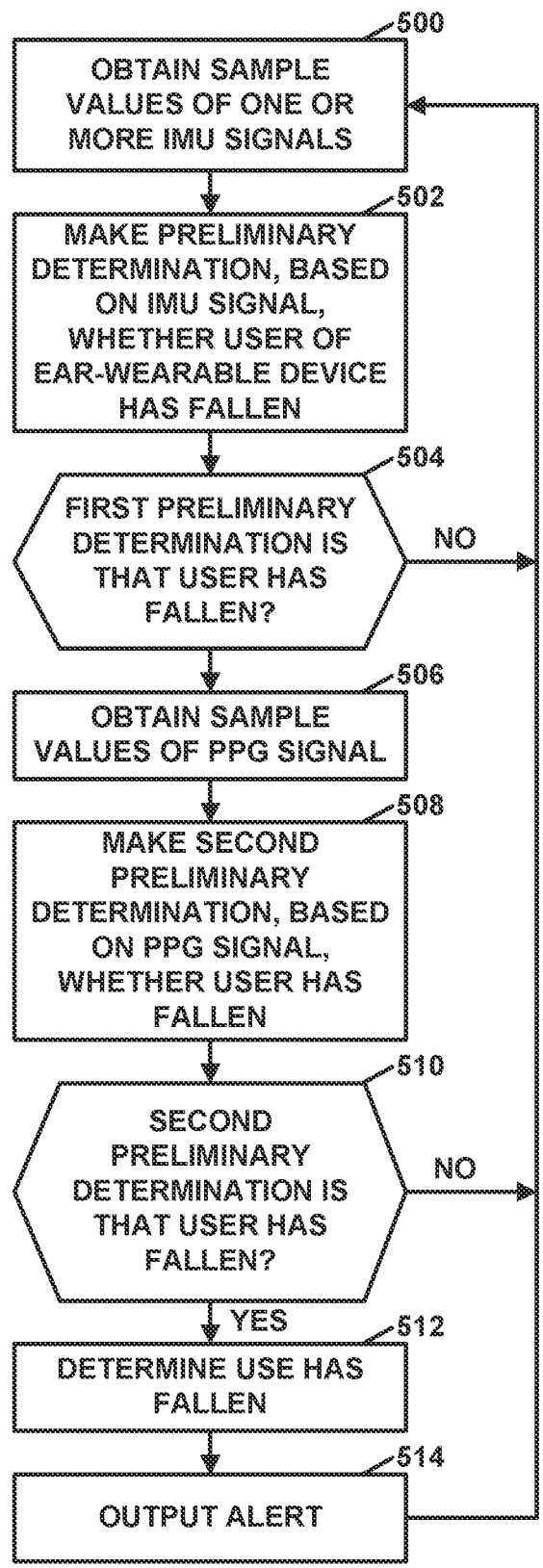
FIG. 5 is a flowchart of a third example operation of the disclosure.

FIG. 5 is a flowchart of a third example operation of the disclosure. In the example of FIG. 5, fall detection processor 120 may obtain sample values of one or more IMU signals (500). Additionally, in the example of FIG. 5, fall detection processor 120 may make a first preliminary determination that the user has fallen based on sample values of the one or more IMU signals (502). For instance, fall detection processor 120 may make the first preliminary determination in the manner described in examples provided elsewhere in this disclosure for determining whether the user has fallen based on signal values of the one or more IMU signals. If the first preliminary determination is that the user has not fallen ("NO" branch of 504), fall detection processor 120 may repeat actions (500) and (502). However, if the first preliminary determination is that the user has fallen ("YES" branch of 504), fall detection processor 120 may obtain sample values of the PPG signal generated by PPG sensor 112 (506).

Additionally, fall detection processor 120 may make a second preliminary determination that the user has fallen based on the sample values of the PPG signal (508). Thus, in the example of FIG. 5, fall detection processor 120 may make the second preliminary determination in response to the first preliminary determination being that the user has fallen. In other examples, this may be reversed. Fall detection processor 120 may make the second preliminary determination in the manner described in examples provided elsewhere in this disclosure for determining whether the user has fallen based on sample values of the PPG signal.

If the second preliminary determination is that the user has not fallen ("NO" branch of 510), fall detection processor 120 may repeat actions (500) through (508), as needed. If the second preliminary determination is that the user has fallen ("YES" branch of 510), fall detection processor 120 may determine that the user has fallen based on both the first preliminary determination and the second preliminary determination being that the user has fallen (512). Accordingly, fall detection processor 120 may then cause ear-wearable device 100 to output an alert (514). Fall detection processor 120 may cause ear-wearable device 100 to output the alert in accordance with any of the examples provided elsewhere in this disclosure.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processing circuits to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, cache memory, or any other medium that can be used to store desired program code in the form of instructions or data structures and that can be accessed by a computer. Also, any connection may be considered a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transitory, tangible storage media. Combinations of the above should also be included within the scope of computer-readable media.

Functionality described in this disclosure may be performed by fixed function and/or programmable processing circuitry. For instance, instructions may be executed by fixed function and/or programmable processing circuitry. Such processing circuitry may include one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. Processing circuits may be coupled to other components in various ways. For example, a processing circuit may be coupled to other components via an internal device interconnect, a wired or wireless network connection, or another communication medium.

Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

The invention claimed is:

1. An ear-wearable device comprising:
 a photoplethysmography (PPG) sensor configured to generate a PPG signal over a time window beginning prior to a fall, wherein the PPG signal is correlated with a local blood perfusion of a user; and
 one or more processors configured to determine, based on sample values of the PPG signal generated by the PPG sensor, that the user of the ear-wearable device has fallen based on the signal from the PPG sensor indicating that the local blood perfusion of the user has risen by a threshold amount for a sustained period of time.

2. The ear-wearable device of claim 1, wherein during wear of the ear-wearable device, the PPG sensor is located inside an ear canal of the user of the ear-wearable device.

3. The ear-wearable device of claim 1, wherein the one or more processors are configured to:
 determine a DC component of the PPG signal; and
 determine whether the DC component of the PPG signal has changed in a particular direction by a threshold amount within a time window.

4. The ear-wearable device of claim 1, further comprising:
an inertial measure unit (IMU),
 wherein the one or more processors are configured to determine, based on the sample values of the PPG signal and based on sample values of one or more IMU signals generated by the IMU, whether the user of the ear-wearable device has fallen.

5. The ear-wearable device of claim 4, wherein the one or more processors are configured such that, as part of determining whether the user of the ear-wearable device has fallen, the one or more processors:
 make a first preliminary determination that the user has fallen based on the sample value of the one or more IMU signals;
 make a second preliminary determination that the user has fallen based on the sample values of the PPG signal; and
 determine that the user has fallen based on both the first preliminary determination and the second preliminary determination being that the user has fallen.

6. The ear-wearable device of claim 5, wherein the one or more processors are configured to make the second preliminary determination in response to the first preliminary determination being that the user has fallen.

7. The ear-wearable device of claim 1, wherein the one or more processors are configured to cause the ear-wearable device to output an alert in response to determining that the user has fallen.

8. The ear-wearable device of claim 7, further comprising a wireless communication system, and
 wherein to cause the ear-wearable device to output the alert, the one or more processors are configured to cause the wireless communication system to wirelessly send an alert message to a computing device.

9. The ear-wearable device of claim 1, wherein the one or more processors are configured to store a first PPG value corresponding to when the user is standing and store a second PPG value corresponding to when the user is lying prone, and wherein the threshold amount is based on a difference between the first PPG value and the second PPG value.

10. A method for detecting whether a user of an ear-wearable device has fallen, the method comprising:
 generating, by a photoplethysmography (PPG) sensor of the ear-wearable device, a PPG signal over a time window beginning prior to a fall;
 obtaining, by one or more processors of the ear-wearable device, sample values of the PPG signal generated by the PPG sensor;
 determining, by the one or more processors, based on the sample values of the PPG signal, that the user of the ear-wearable device has fallen if a DC component of the PPG signal changes over a threshold value within the time window; and
 outputting, by the ear-wearable device, an alert in response to determining that the user has fallen.

11. The method of claim 10, wherein during wear of the ear-wearable device, the PPG sensor is located inside an ear canal of the user of the ear-wearable device.

12. The method of claim 10,
 wherein the signal from the PPG sensor is correlated with a local blood perfusion of the user, and
 wherein determining whether the user has fallen comprises determining, by the one or more processors, that the user has fallen based on the sample values of the PPG signal indicating that the local blood perfusion of the user has risen by a threshold amount within a threshold amount of time.

13. The method of claim 10, further comprising:
 determining, by the one or more processors, whether the DC component of the PPG signal has changed in a particular direction by a threshold amount within the time window.

14. The method of claim 10,
 wherein the ear-wearable device comprises an inertial measure unit (IMU), and wherein determining whether the user of the ear-wearable device has fallen comprises determining, by the one or more processors, based on the sample values of the PPG signal and based on sample values of one or more IMU signals from the IMU, whether the user of the ear-wearable device has fallen.

15. The method of claim 14, wherein determining whether the user of the ear-wearable device has fallen comprises:
    making, by the one or more processors, a first preliminary determination that the user has fallen based on the sample values of the one or more IMU signals;
    making, by the one or more processors, a second preliminary determination that the user has fallen based on the sample values of the PPG signal; and
    determining, by the one or more processors, that the user has fallen based on both the first preliminary determination and the second preliminary determination being that the user has fallen.

16. The method of claim 14, wherein making the second preliminary determination comprises making, by the one or more processors, the second preliminary determination in response to the first preliminary determination being that the user has fallen.

17. The method of claim 10, wherein causing the ear-wearable device to output the alert comprises causing, by the one or more processors, the wireless communication system to wirelessly send an alert message to a computing device.

18. The method of claim 10, further comprising:
    calculating differences between DC component values of the PPG signal corresponding to successive time windows; and
    determining whether a user of the ear-wearable device has fallen if any of the differences between the DC component values of the PPG signal is greater than a particular threshold value.

* * * * *